United States Patent [19]

Hendrickx et al.

[11] Patent Number: 6,121,460
[45] Date of Patent: Sep. 19, 2000

[54] PROCESS FOR THE PREPARATION OF AN OPTICALLY ACTIVE INDOLINE-2-CARBOXYLIC ACID OR DERIVATIVE THEREOF

[75] Inventors: Andreas J. J. Hendrickx, Venlo; Thijs Kuilman, Venlo-Blerick, both of Netherlands

[73] Assignee: DSM N.V., Heerlen, Netherlands

[21] Appl. No.: 09/249,025

[22] Filed: Feb. 12, 1999

[30] Foreign Application Priority Data

Feb. 13, 1998 [NL] Netherlands ............... 1008302

[51] Int. Cl.[7] .................. C07D 209/12; C07D 209/26
[52] U.S. Cl. .................. 548/491; 548/492; 548/493; 562/473; 560/19
[58] Field of Search .................... 548/491, 492, 548/493; 562/473; 560/19

[56] References Cited

U.S. PATENT DOCUMENTS

| | | | |
|---|---|---|---|
| 4,520,205 | 5/1985 | Buzby, Jr. ............. | 548/491 |
| 4,665,087 | 5/1987 | Vlattas ................ | 514/419 |
| 4,824,964 | 4/1989 | Miyata et al. ......... | 548/490 |
| 5,149,821 | 9/1992 | Moore et al. .......... | 548/215 |
| 5,166,361 | 11/1992 | Zepp .................. | 548/533 |

FOREIGN PATENT DOCUMENTS 0 171 616   2/1986   European Pat. Off. .

OTHER PUBLICATIONS

Tsukamoto, Masatoshi et al., Abstract No. 60525w, "Optical Resolution of (RS)–1–Acetyl–2–Carboxylic Acid", Chemical Abstracts, Aug. 18, 1986, vol. 105, No. 7, Columbus, Ohio, US.

*Primary Examiner*—Joseph McKane
*Assistant Examiner*—Jane C. Oswecki
*Attorney, Agent, or Firm*—Pillsbury Madison & Sutro LLP

[57] ABSTRACT

Process for the preparation of an optically active N-acyl-indoline-2-carboxylic acid in which a mixture of enantiomers of N-acyl-indoline-carboxylic acid is contacted with an optically active resolving agent and the optically active N-acyl-indoline-2-carboxylic acid is liberated from the resulting diastereomeric salt, as resolving agent use being made of a compound of formula 1, where $R_1$ represents an alkyl group and $R_2$ a hetero-aryl group or where $R_1$ and $R_2$ together with the C atoms to which they are bound form a cycloalkyl group with 5–8 C atoms, fused with a hetero-aryl group. Preferably, a mixture of enantiomers of an N-acyl-indoline-2-carboxylic acid is prepared in a process comprising the steps of Fischer indole cyclization of a 2-phenylhydrazone propionic acid or a derivative thereof in the presence of an acid catalyst, if necessary hydrolysis of the derivative to the corresponding acid, acylation at the N-position and reduction of the indole compound to the corresponding indoline compound, after which the resulting N-acyl-indoline-2-carboxylic acid is subjected to the resolution. The 2-phenylhydrazonopropionic acid or a derivative thereof is preferably obtained from phenylhydrazine and pyruvic acid or the corresponding derivative thereof.

13 Claims, No Drawings

PROCESS FOR THE PREPARATION OF AN OPTICALLY ACTIVE INDOLINE-2-CARBOXYLIC ACID OR DERIVATIVE THEREOF

FIELD OF THE INVENTION

The invention relates to a process for the preparation of an optically active N-acyl-indoline-2-carboxylic acid in which a mixture of enantiomers of N-acyl-indoline-2-carboxylic acid is contacted with an optically active resolving agent and the optically active N-acyl-indoline-2-carboxylic acid is liberated from the diastereomeric salt obtained.

BACKGROUND TECHNOLOGY

A process is disclosed JP-A61030572 which N-isopropyl-phenylanlaninol is used as a resolving agent.

A drawback of the known process is that a recrystallization is needed to achieve an e.e. (enantiomeric excess) of more than 95% (95.4%).

SUMMARY OF THE INVENTION

The process according to the present invention does not suffer from the above-mentioned drawback.

According to the invention this is achieved when as resolving agent use is made of a compound of formula 1

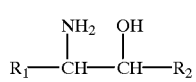

where $R_1$ represents a (1–20C) alkyl group and $R_2$ a (4–20C) (hetero)aryl group or where $R_1$ and $R_2$ together with the C atoms to which they are bound form a cycloalkyl group with 5–8 C atoms, fused with a (4–20C)(hetero) aryl group.

It has been found that optically active indoline-2-carboxylic acid with a high e.e. can be prepared in a high yield with the resolving agents according to the invention.

DETAILED DESCRIPTION OF THE INVENTION

A process embodiment of the present invention concerns preparation of an optically active N-acyl-indoline-2-carboxylic acid in which a mixture of enantiomers of N-acyl-indoline-2-carboxylic acid is contacted with an optically active resolving agent and the optically active N-acyl-indoline-2-carboxylic acid is liberated from the resulting diastereomeric salt. The resolving agent is a compound represented by the formula (1) above, in which $R_1$ represents a alkyl group and $R_2$ represents a (hetero) aryl group, or $R_1$ and $R_2$, together with the carbon atoms to which each are bound, forms a cycloalkyl group having 5 to 8 carbon atoms, fused with a (hetero) alkyl group.

Examples of suitable resolving agents are compounds according to formula 1, where $R_1$ represents an alkyl group with 1–20 C atoms, which may be substituted with, for instance, one or more nitro, mercapto, hydroxy, alkyl, aryl, alkoxy, alkylamino, thio groups or halogens, and where $R_2$ represents a (hetero) aryl group, for instance a substituted or unsubstituted phenyl, naphthyl, pyridyl or pyrimidyl group, which may be substituted with, for instance, one or more amino, nitro, mercapto, hydroxy, alkyl, aryl, alkoxy, alkylamino, thio groups or halogens or where $R_1$ and $R_2$ together with the C atoms to which they are bound form a cycloalkyl group with fused to it a (hetero)aryl group, which may for instance be substituted with one or more amino, nitro, mercapto, hydroxy, alkyl, aryl, alkoxy, alkylamino, thio groups or halogens. Preferably, $R_2$ stands for a substituted or unsubstituted phenyl group and $R_1$ for a hydroxyalkyl group or $R_1$ and $R_2$ together with the C atoms to which they are bound form a cyclic alkyl group with fused to it a (hetero)aryl group, for instance (1R,2R) or (1S,2S)- 1-(4-nitrophenyl)-2-amino-1,3-propanediol or (1R,2R) or (1S, 2S)-1-phenyl-2-amino-1,3-propanediol.

As resolving agent use can also very suitably be made of a mixture of resolving agents of different chemical compositions, for instance a mixture of (1R,2R)-1-(4-nitrophenyl)-2-amino-1,3-propanediol and (1S,2S)-1-phenyl-2-amino-1,3-propanediol. The resolving agents used in the mixture of optically active resolving agents are preferably each present in the mixture in optically active form.

The acyl groups in N-acyl-indoline-2-carboxylic acid can for instance be the groups R—C(O)— with R being alkyl, alkoxy, aryl or aryloxy, for instance with 1–10 C-atoms; preferably with R being methyl.

The temperature at which the resolution is effected preferably lies between 20 and 150° C., in particular between 50 and 100° C. The pressure at which the resolution is carried out is not very critical. For practical reasons the resolution is preferably carried out at atmospheric pressure.

Examples of suitable solvents that can be used in the resolution are water, alcohols, in particular methanol, ethanol, isopropanol. Preferably, as solvent use is made of an alcohol—optionally mixed with water—for instance ethanol or a mixture of alcohols—optionally mixed with water—for instance a methanol/ethanol mixture. It is also possible to effect the resolution starting from a slurry. The amount of solvent, the temperature and the number of equivalents of optically active resolving agent are preferably chosen so that the mixture of solvent, optically active resolving agent and enantiomer mixture to be resolved is (just) in solution. For a better reproducible crystallization preferably grafts of the salt of the resolving agent and the desired enantiomer of N-acyl-indoline-2-carboxylic acid are added, as a result of which in practice usually a better crystal size distribution of the diastereomeric salt is obtained.

The amount of resolving agent to be used is preferably larger than 1 equivalent calculated on the amount of the desired enantiomer present in the mixture of enantiomers. When the starting mixture is a racemic mixture, the amount of resolving agent to be used is preferably between 0.5 and 1 equivalent, calculated on the total amount of the mixture of enantiomers to be resolved, in particular between 0.55 and 0.70 equivalent, more in particular between 0.65 and 0.7 equivalent. The enantiomeric purity of the resolving agent is preferably chosen as high as possible, in particular higher than 90%, more in particular higher than 95%.

In principle it is, if desired, possible to recover and reuse the resolving agent, for instance via extraction or crystallization.

Via desalting the optically active N-acyl-indoline-2-carboxylic acid can subsequently be obtained from the diastereomeric salt in a generally known way, for instance through treatment with an acid, for instance a mineral acid, in particular diluted aqueous hydrochloric acid or sulphuric acid. The temperature can, for instance, be chosen between 20 and 100° C., preferably between 60 and 70° C., after which the optically active N-acyl-indoline-2-carboxylic acid can be recovered for instance through cooling.

The optically active N-acyl-indoline-2-carboxylic acid can then be converted into optically active indoline-2-carboxylic acid through deacylation, for instance with the aid of an acid or a base. If desired, desalting and deacylation can be carried out in one step, that is, without isolation of the intermediate product.

The undesired enantiomer of the N-acyl-indoline-2-carboxylic acid can if desired, after recovery from the mother liquor, be subjected to a racemization, for instance as described in JP-A-61083159 and in JP-A-02225463.

The racemic mixture of enantiomers can very suitably be prepared via Fischer indole cyclization of a 2-phenylhydrazonopropionic acid or a derivative thereof, for instance the free acid or an ester, in particular an alkyl or aryl ester, more in particular the ethyl ester; optionally hydrolysis to yield the free acid; N-acylation and reduction of the indole-2-carboxylic acid or the derivative thereof to the corresponding indoline-2-carboxylic acid or the derivative thereof. The order of the steps is not particularly important. Preferably, the ethyl ester is started from in the Fischer indole cyclization, then the ester is hydrolyzed to yield the free acid, subsequently the acid is acylated to N-acyl-indole-2-carboxylic acid and finally the N-acyl-indole-2-carboxylic acid is reduced to the corresponding N-acyl-indoline-2-carboxylic acid. The invention therefore also relates to a process for the preparation of optically active indoline-2-carboxylic acid derivatives thereof starting from 2-phenylhydrazono-propionic acid or derivatives thereof. It has been found that optically active indoline-2-carboxylic acid with a high enantiomeric excess can be prepared with a high efficiency in this way. (S)-indoline-2-carboxylic acid is an intermediate in the preparation of perindopril.

The Fischer indole cyclization is carried out in the presence of an acid catalyst, for instance a mineral acid, in particular, HBr; a sulphonic acid, in particular methane sulphonic acid and p-toluene sulphonic acid; $BF_3O(Et)_2$; metal halides, in particular $ZnCl_2$.

Preferably, the 2-phenylhydrazonopropionic acid or derivative thereof is prepared in situ from phenylhydrazine and pyruvic acid or a pyruvic acid ester through condensation in a suitable organic solvent, for instance glacial acetic acid, benzene, toluene, the water formed being removed through (azeotropic) distillation. However, isolation of the 2-phenylhydrazonopropionic acid or derivative thereof is also possible, following which the hydrazone obtained is used in the Fischer indole cyclization.

The reaction medium of the Fischer indole cyclization is preferably kept as water-free as possible, since water produces undesirable side reactions, in particular hydrolysis of the 2-phenylhydrazonopropionic acid or derivative thereof.

Preferably, the ethyl ester is used as derivative of 2-phenylhydrazonopropionic acid in connection with the stability of the 2-phenylhydrazonopropionic acid or derivative thereof, the solubility of the intermediates and the product during the Fischer indole cyclization in apolar solvents, for instance aromatic hydrocarbons, in particular benzene and toluene, and the availability of the pyruvic acid ester.

The geometry of the 2-phenylhydrazonopropionic acid or derivative thereof (syn/anti) has little effect on the yield of the Fischer indole cyclization, for under the reaction conditions isomerization takes place by the action of the acid catalyst.

Suitable solvents are, for instance, carboxylic acids, in particular acetic acid, aromatic hydrocarbons, in particular benzene, toluene, xylene or mixtures thereof, or alcohols, in particular the alcohol corresponding to the ester used, for instance ethanol when the ethyl ester is used.

Preferably, for safety reasons and to avoid undesirable oxidation reactions use is made of a nitrogen atmosphere.

The reaction temperature of the Fischer indole cyclization is preferably in the range of 15–140° C., in particular 15–50° C., more in particular 20–35° C., this being a compromise between stability of the reagents/product, selectivity, and rate of the Fischer indole cyclization.

The amount of acid catalyst to be used is preferably in the range of 1–1.5 equivalents, preferably 1–1.3 equivalents. The minimum amount needed is 1 equivalent, since salt formation with the $NH_3$ formed renders the catalyst inactive.

To prevent subsequent reactions of the indole-2-carboxylic acid derivative with the pyruvic acid or derivative thereof at the free 3-position of the indole ring, preferably a small excess of phenylhydrazine relative to pyruvic acid or derivative thereof is used, in the case of in situ preparation of the 2 phenylhydrazonopropionic acid or derivative thereof.

The hydrolysis of the indole-2-carboxylic acid ester with water is preferably carried out in the presence of a base, in particular sodium or potassium hydroxide, or, when the hydrolysis is carried out in a two-phase system, with the aid of a phase transfer catalyst, for instance tetrabutyl ammoniumbromide and a base, in particular the above-mentioned bases. If desired, the hydrolysis can be effected on the non-isolated indole-2-carboxylic acid ester after working up of the Fischer indole cyclization.

The acylation of the indole-2-carboxylic acid or derivative thereof or the indoline-2-carboxylic acid or derivative thereof with a suitable acylation agent preferably takes place in a basic organic environment. If desired, an acylation catalyst can be used, for instance pyridine or 4-dimethylaminopyridine. As acylation agent use can be made, for instance, of acyl chlorides, in particular acetyl chloride and trifluoroacetyl chloride, anhydrides, in particular acetic anhydride and alkoxycarbonyl chlorides, in particular tert.-butoxycarbonyl chloride. Suitable bases that can be used in the acylation are, for instance, carboxylic acid salts, in particular sodium acetate and potassium acetate, amines, in particular triethylamine, hydroxides, in particular sodium hydroxide in combination with a phase transfer catalyst. As solvent the customary solvents can be used, for instance dimethylformamide (DMF), dichloromethane, methylacetate, tertbutyl-acetate, methyl-tert.butylether (MTBE), acetic anhydride and acetone.

The temperature at which the acylation takes place preferably lies between −5° C. and the reflux temperature of the chosen solvent, in particular between 0 and 25° C., more in particular between 0 and 5° C.

The amount of base to be used preferably lies between 1 and 2 equivalents, calculated on the amount of the compound to be acylated, in particular between 1.25 and 1.8 equivalents. Preferably, the solvent, the base and the catalyst are supplied successively, following which the indole-2-carboxylic acid or derivative thereof and lastly the acylation agent are dosed.

Starting from indole-2-carboxylic acid preferably the combination acetone, triethylamine, 4-dimethylaminopyridine and acetic anhydride is used.

The reduction of the—optionally acylated—indole compound to the corresponding indoline compound can, for instance, be effected by means of chemical reduction, catalytic hydrogenation or transfer hydrogenation. Preferably, a catalytic hydrogenation is carried out with the aid of $H_2$ and a noble metal catalyst, starting from N-acyl-indole-2-carboxylic acid.

EXAMPLE I

Fischer indole cyclization to indole-2-carboxylic acid ethyl ester.

A solution of 59 g ethylpyruvate in 500 ml toluene was heated to reflux upon which 55 g phenylhydrazine was dosed. Using a Dean-Stark apparatus approx. 8 ml water was distilled off. After cooling 52.5 g HBr gas was introduced at 15–20° C. in 1 hour, which was followed by stirring for 1 hour at 15° C. 150 ml water was added and heated to 55° C. After separation of the water phase the organic phase was re-extracted with 150 ml water of 50° C. 250 ml toluene was distilled off from the organic phase and cooled to 20° C. 400 ml isododecane was added and the solid formed was filtered off and washed three times with 30 ml isododecane. Upon drying 71.5 g indole-2-carboxylic acid ethylester was obtained, corresponding to a yield of 75.7%. Purity 95.5% w/w (HPLC).

EXAMPLE II

Fischer indole cyclization to indole-2-carboxylic acid.

At 40–55° C. 7 ml pyruvic acid was dosed to a solution of 10 ml phenylhydrazine in 100 ml glacial acetic acid. After cooling to 0° C. the hydrazone that had crystallized out was filtered off and washed with glacial acetic acid. This yielded 14.3 g yellow 2-phenylhydrazonopropionic acid, corresponding to an 80% yield. 1.75 ml 33% HBr in glacial acetic acid was dosed to 1.78 g of this hydrazone in 50 ml glacial acetic acid, which was followed by 2 hours' stirring at 40° C. The reaction mixture was evaporated using the rotavapor and the residue was dissolved in NaOH aq. After neutralization to pH=2 the precipitate formed was filtered off and washed with water. This yielded 0.85 g indole-2-carboxylic acid, corresponding to a 53% yield.

EXAMPLE III

Hydrolysis to indole-2-carboxylic acid.

A mixture of 189 g indole-2-carboxylic acid ethylester, 750 ml water and 88 g 50% NaOH was heated to reflux, upon which all the material was in solution. After 15 minutes' subsequent stirring, cooling to 50° C. took place and 125 g 33% HCl aq was slowly dosed to pH 2. After cooling to 15° C. the solid was filtered off, washed with water and dried to the air. This yielded 159.1 g indole-2-carboxylic acid, corresponding to a 98.8% yield. Purity 99.6% w/w (titration with sodium hydroxide). Melting point 204.5–205.5° C.

EXAMPLE IV

Acetylation to N-acetyl-indole-2-carboxylic acid.

At 40–50° C. 64.4 g indole-2-carboxylic acid was dosed to a solution of 0.48 g 4-dimethylaminopyridine and 70 ml triethylamine in 100 ml acetone, followed by stirring for 15 minutes at 45° C. After cooling to 20° C. 42 ml acetic anhydride was dosed at 20–25° C., which was followed by 45 minutes' stirring. The mixture obtained was poured out onto a mixture of 52 ml 33% HCl aq, 100 g ice and 160 ml water and stirred for 1 hour at 15° C. The solid was filtered off, washed with ice water and dried. This yielded 74.7 g N-acetyl-indole-2-carboxylic acid, corresponding to a yield of 92.6%.

EXAMPLE V

Hydrogenation to N-acetyl-indoline-2-carboxylic acid.

A mixture of 60 g N-acetyl-indole-2-carboxylic acid, 360 ml glacial acetic acid and 3 g 10% Pd/C was heated to 75° C., following which nitrogen was passed through for 30 minutes. Hydrogen was introduced up to the point where no further hydrogen was taken up (after 5.5 hours). The Pd/C was filtered off over dicalite. The filtrate was evaporated to a residue of approx. 60 grams. 300 ml tert.butylacetate was added and heated to reflux. After cooling to 10° C. the solid was filtered off, washed with tert.butylacetate and dried to the air. This yielded 54 g N-acetyl-indoline-2-carboxylic acid, corresponding to a yield of 87.8%.

EXAMPLE VI

Resolution of N-acetyl-indoline-2-carboxylic acid with (+)(1S,2s)-1-phenyl-2-amino-1,3-propanediol.

100 g N-acetyl-indoline-2-carboxylic acid (purity 96.5%) was dissolved in 835 ml of a mixture containing 90% ethanol (EtOH), 5% water and 5% methanol (MeOH), with heating to 60° C., and with mechanical stirring. 54.4 g/0.69 eq. (1S,2S)-1-phenyl-2-amino-1,3-propanediol ($[\alpha]^{20}_D$=+25.7° (c=1, MeOH)) was dosed in portions in 30 min. at 60° C. At the end spontaneous crystallization of the salt took place. After 30 minutes' subsequent stirring at 60–66° C., cooling to 15° C. took place, followed by another 30 minutes' stirring. After filtration over a P4 glass filter, three washings with 120 ml EtOH took place. After air-drying, 68.9 g off-white (S)-N-acetyl-indoline-2-carboxylic acid-(1S,2S)-1-phenyl-2-amino-1,3-propanediol salt was obtained, corresponding to a yield of 37.8%. Enantiomeric excess=96.3% (chiral HPLC).

EXAMPLE VII

Resolution of N-acetyl-indoline-2-carboxylic acid with (−)(1R,2R)-1-(4-nitrophenyl)-2-amino-1,3-propanediol.

200 g N-acetyl-indoline-2-carboxylic acid (purity 96.5%) was dissolved in 1760 ml of a mixture containing 90% EtOH, 5% water and 5% MeOH, with heating to 76° C., and with mechanical stirring. 138 g/0.69 eq (1R,2R)-1-(4-nitrophenyl)-2-amino-1,3-propanediol (99.5% chemically pure, $[a]^{20}_D$=−28.5° (c=0.4, 1N HCl)) was dosed in portions in 30 min. at 73–76° C. After cooling to 70° C., grafting with 1 g S-salt took place, followed by cooling to 15° C. in 3 hours and 30 minutes' subsequent stirring. After filtration over a P4 glass filter, 3 washings with 200 ml EtOH took place. After air-drying, 158.1 g yellow (S)-N-acetyl-indoline-2-carboxylic acid-(1R,2R)-1-(4-nitrophenyl)-2-amino-1,3-propanediol salt was obtained, corresponding to a yield of 40.3%. Enantiomeric excess=99.0% (chiral HPLC).

EXAMPLE VIII

Resolution of N-acetyl-indoline-2-carboxylic acid with (−)(1R,2R)-1-(4-nitrophenyl)-2-amino-1,3-propanediol in absolute ethanol.

25 g N-acetyl-indoline-2-carboxylic acid (purity 96.5%) was dissolved in 300 ml absolute EtOH while being heated to 70° C. and with mechanical stirring. 17.25 g/0.69 eq. (1R,2R)-1-(4-nitrophenyl)-2-amino-1,3-propanediol (99.5% chemically pure, $[a]^{20}_D$=−28.5° (c=0.4, 1N HCl)) was dosed in portions in 30 min. at 66–70° C. Spontaneous crystallization occurred. After 30 minutes' subsequent stirring at 69–70° C., cooling to 18° C. took place in 2.5 hours, followed by another 30 minutes' stirring. After filtration over a P4 glass filter 3 washings with 30 ml EtOH took place. After air-drying, 20.7 g yellow (S)-N-acetyl-indoline-2-carboxylic acid-(1R,2R)-1-(4-nitrophenyl)-2-amino-1,3-propanediol salt was obtained, corresponding to a yield of 42.0%. Enantiomeric excess=95.9% (chiral HPLC).

EXAMPLE IX

Resolution of N-acetyl-indoline-2-carboxylic acid with (+)-(1S,2R)-Norephedrine ((+)-(1S,2R)-1-phenyl-2-amino-1-propanol).

2,05 g N-acetyl-indoline-2-carboxylic acid (purity 99%) was dissolved in 8.5 mol of a mixture containing 90% EtOH, 5% water and 5% methanol, with heating to 78° C., and with mechanical stirring. 1.51 g/l eq. (+)-(1S,2R)-Norephedrine ($[\alpha]^{20}_D$=+40° C. (C=7, 1N HCl) was added al once at 78° C. followed by rinsing with 1 ml of a mixture containing 90% EtOH, 5% water and 5% MeOH.

The solution obtained was cooled in 1 hour to 37° C. and grafted with approximately 5 mg R-salt, after which crystallisation started slowly. The slurry was further cooled to 22° C. After filtration over a glass filter, 2 washings with 5 ml of a mixture containing 90% EtOH, 5% water and 5% MeOH and drying at 40° C., 0.82 g white (R)-N-acetyl-indoline-2-carboxylic acid-(1S,2R)-norephedrine salt was obtained (probably as methanol solvate). The content of (R)-N-acetyl-indoline-2-carboxylic acid was 51.8 weight % (HPLC) corresponding to a yield of 20.9%. Enantiomeric excess =95.5% (chiral HPLC).

EXAMPLE X
Desalting to (S)-N-acetyl-indoline-2-carboxylic acid.

1.835 kg dried (S)-N-acetyl-indoline-2-carboxylic acid-(1R,2R)-1-(4-nitrophenyl)-2-amino-1,3-propanediol salt was dosed in portions to 2.64 1 2N HCl aq (1.13 eq HCl) with heating to 60° C., followed by 30 minutes' stirring at 60–70° C. After cooling to 20° C., filtration on an FIBA, washing with 2×0.7 1 water and drying, 871 g white (S)-N-acetyl-indoline-2-carboxylic acid was obtained, corresponding to a yield of 96.5%. Enantiomeric excess=99.9% (chiral HPLC).

EXAMPLE XI
Deacetylation of (S)-N-acetyl-indoline-2-carboxylic acid to (S)-indoline-2-carboxylic acid.

With heating at 20–70° C. 712.3 g wet (S)-N-acetyl-indoline-2-carboxylic acid (443 g based on dry weight) was added in portions to 958 ml 5N HCl aq, followed by rinsing with 100 ml water. The slurry was heated to about 103° C. (reflux) and refluxed for 45 minutes. After cooling to 70° C., the solution was decoloured using Norit. After filtration 50% NaOH aq was used at 20–25° C. to set the pH of the filtrate at 4.

The crystals were filtered off and washed with 3×400 and 3×350 ml water. Upon drying, 306.2 g white (S)-indoline-2-carboxylic acid was obtained, corresponding to a yield of 87%. Enantiomeric excess>99.9% (chiral HPLC). Content= 99.4% w/w (titration with sodium hydroxide). $[\alpha]^{20}_D$=−117.2° (c=1, 2N HC1).

What is claimed is:

1. A process for the preparation of an optically active N-acyl-indoline-2-carboxylic acid in which a mixture of enantiomers of N-acyl-indoline-2-carboxylic acid is contacted with at least one optically active resolving agent and the optically active N-acyl-indoline-2-carboxylic acid is liberated from the resulting diastereomeric salt, wherein the resolving agent comprises at least one compound represented by formula 1

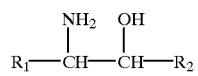

(1)

wherein $R_1$ represents an optionally substituted alkyl group and $R_2$ an optionally substituted (hetero) aryl group or in which $R_1$ and $R_2$ together with the C atoms to which they are bound form an optionally substituted cycloalkyl group with 5–8 C atoms, fused with a (hetero) aryl group.

2. A process according to claim 1, wherein $R_1$ represents hydroxymethyl and $R_2$ represents a substituted or unsubstituted phenyl group.

3. A process according to claim 2, wherein $R_2$ represents p-nitrophenyl.

4. A process according to any one of claims 1–3, wherein a mixture of resolving agents is used.

5. A process according to any one of claims 1–3, wherein the N-acyl-indoline-2-carboxylic acid is N-acetyl-indoline-2-carboxylic acid and the mixture of enantiomers comprises N-acetyl-indoline-2-carboxylic acid.

6. A process according to claim 1, wherein the process further comprises deacylating the optically active N-acyl-indoline-2-carboxylic acid.

7. A process according to claim 1, wherein the process further comprises esterifying the optically active indoline-2-carboxylic acid.

8. A process according to claim 1, wherein the process further comprises first preparing the mixture of enantiomers of an N-acyl-indoline-2-carboxylic acid in a process comprising Fischer indole cyclization of a 2-phenylhydrazono-propionic acid or a derivative thereof in the presence of an acid catalyst; hydrolysis of the derivative, if present, to the corresponding acids; acylation at the N-position; and reduction of the indole compound to the corresponding indoline compound, after which the resulting N-acyl-indoline-2-carboxylic acid is subjected to a resolution according to claim 1.

9. A process for the preparation of an optically active N-acyl-indoline-2-carboxylic acid comprising:

preparing a mixture of enantiomers of an N-acyl-indoline-2-carboxylic acid in a process comprising Fischer indole cyclization of a 2-phenylhydrazono-propionic acid or a derivative thereof in the presence of an acid catalyst comprising HBr;

hydrolyzing the derivative, if present, to the corresponding acid, acylating at the N-position and reducing the indole compound to a corresponding N-acyl-indoline-2-carboxylic acid, resolving N-acyl-indoline-2-carboxylic acid with a mixture of enantiomers of N-acyl-indoline-2-carboxylic acid by contact with at least one optically active resolving agent, and liberating an optically active N-acyl-indoline-2-carboxylic acid from a resulting diastereomeric salt, wherein the resolving agent comprises at least one compound represented by formula 1

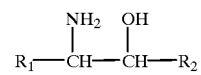

(1)

wherein $R_1$ represents an optionally substituted alkyl group and $R_2$ an optionally substituted (hetero) aryl group or in which $R_1$ and $R_2$ together with the C atoms to which they are bound form a cycloalkyl group with 5–8 C atoms, fused with a (hetero) aryl group.

10. A process according to claim 8 or 9, wherein the cyclization is of i) 2-phenylhydrazono-propionic acid prepared from phenylhydrazine and pyruvic acid or ii) a derivative of 2-phenylhydrazono-propionic acid prepared from phenylhydrazine and a pyruvic acid derivative corresponding to the 2-phenylhydrazono-propionic acid derivative, wherein the derivative is a member selected from the group consisting of a free acid and an ester.

11. A for the preparation of an optically active N-acyl-indoline-2-carboxylic acid comprising:

preparing a mixture of enantiomers of an N-acyl-indoline-2-carboxylic acid in a process comprising Fischer indole cyclization of a 2-phenylhydrazono-propionic acid or a derivative thereof in the presence of an acid catalyst comprising HBr, wherein the 2-phenylhydrazono-propionic acid is prepared in situ from phenylhydrazine and pyruvic acid or the derivative of 2-phenylhydrazono-propionic acid is prepared from phenylhydrazine and a pyruvic acid derivative corresponding to the 2-phenylhydrazono-propionic acid derivative;

hydrolyzing the derivative, if present, to a corresponding acid, acylating at the N-position and reducing a resulting indole compound to a N-acyl-indoline-2-carboxylic acid, resolving the N-acyl-indoline-2-carboxylic acid with a mixture of enantiomers of N-acyl-indoline-2-carboxylic acid by contact with at least one optically active resolving agent, and liberating an optically active N-acyl-indoline-2-carboxylic acid from a resulting diastereomeric salt, wherein the resolving agent comprises at least one compound represented by formula 1

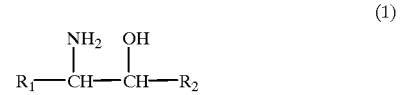

(1)

wherein $R_1$ represents an optionally substituted alkyl group and $R_2$ an optionally substituted (hetero) aryl group or in which $R_1$ and $R_2$ together with the C atoms to which they are bound form an optionally substituted cycloalkyl group with 5–8 C atoms fused with a (hetero) aryl group.

12. A process according to claim 11, wherein cyclization is of an ethyl ester derivative of 2-phenylhydrozonopropionic acid.

13. A process according to claim 12, wherein first an optional hydrolysis takes place, subsequently the acylation, followed by the reduction.

* * * * *